US010206675B2

(12) United States Patent
Shah

(10) Patent No.: US 10,206,675 B2
(45) Date of Patent: Feb. 19, 2019

(54) METHOD AND APPARATUS FOR FABRICATING SELF-RETAINING SUTURES WITH CALIBRATION

(71) Applicant: ETHICON LLC, Guaynabo, PR (US)

(72) Inventor: Nilesh A. Shah, Annandale, NJ (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/636,709

(22) Filed: Jun. 29, 2017

(65) Prior Publication Data
US 2018/0014827 A1 Jan. 18, 2018

Related U.S. Application Data

(60) Provisional application No. 62/361,647, filed on Jul. 13, 2016.

(51) Int. Cl.
| | |
|---|---|
| *G01B 11/14* | (2006.01) |
| *A61B 17/06* | (2006.01) |
| *B26D 3/08* | (2006.01) |
| *B21F 45/00* | (2006.01) |
| *A61B 17/04* | (2006.01) |
| *A61B 17/00* | (2006.01) |

(52) U.S. Cl.
CPC .... *A61B 17/06166* (2013.01); *A61B 17/0401* (2013.01); *B21F 45/00* (2013.01); *B26D 3/08* (2013.01); *G01B 11/14* (2013.01); *A61B 17/0469* (2013.01); *A61B 2017/00526* (2013.01); *A61B 2017/00725* (2013.01); *A61B 2017/06176* (2013.01)

(58) Field of Classification Search
CPC ........ G01B 11/00; G01B 11/14; G01B 3/004; G01N 1/06; G01N 1/42; G02B 27/2214; G02B 3/0025; G02B 3/005; G02B 5/3033
See application file for complete search history.

(56) References Cited

U.S. PATENT DOCUMENTS

| | | | | |
|---|---|---|---|---|
| 3,025,747 | A | * | 3/1962 | Casselman ........... G01B 11/303 250/233 |
| 6,848,152 | B2 | | 2/2005 | Genova et al. |
| 7,225,512 | B2 | | 6/2007 | Genova et al. |
| 7,624,487 | B2 | | 12/2009 | Trull et al. |
| 7,913,365 | B2 | | 3/2011 | Genova et al. |
| 7,996,967 | B2 | | 8/2011 | Genova et al. |
| 7,996,968 | B2 | | 8/2011 | Genova et al. |

(Continued)

FOREIGN PATENT DOCUMENTS

| | | |
|---|---|---|
| WO | WO 2009/115936 A1 | 9/2009 |
| WO | WO 2014/061968 A1 | 4/2014 |

OTHER PUBLICATIONS

European Search Report and Written Opinion dated Oct. 25, 2017 for Application No. EP 17181218.3, 5 pgs.

(Continued)

*Primary Examiner* — Michael P Stafira
(74) *Attorney, Agent, or Firm* — Frost Brown Todd LLC

(57) ABSTRACT

An apparatus and method for improved cutting of self-retaining elements on a suture material, including the use of an improved calibration system. The calibration system includes a light emitting source and light receiving source, emitting light through a blade housing where the blade edge is within the light emitted pathway. The blade housing can be moved in accordance with the calibration information.

18 Claims, 13 Drawing Sheets

(56) References Cited

U.S. PATENT DOCUMENTS

| | | |
|---|---|---|
| 8,011,072 B2 | 9/2011 | Genova et al. |
| 8,015,678 B2 | 9/2011 | Genova et al. |
| 8,020,263 B2 | 9/2011 | Genova et al. |
| 8,028,387 B2 | 10/2011 | Genova et al. |
| 8,028,388 B2 | 10/2011 | Genova et al. |
| 8,032,996 B2 | 10/2011 | Trull et al. |
| 8,225,673 B2 | 7/2012 | D'Agostino |
| 8,615,856 B1 | 12/2013 | Gelbart |
| 8,641,732 B1 | 2/2014 | Goraltchouk et al. |
| 8,875,607 B2 | 11/2014 | Kozlowski |
| 8,926,659 B2 | 1/2015 | Genova et al. |
| 9,068,821 B2 | 6/2015 | Fujimoto |
| 2008/0162073 A1* | 7/2008 | Holecek ............... G01B 11/255 702/150 |
| 2009/0107965 A1* | 4/2009 | D'Agostino ..... A61B 17/06166 219/121.69 |
| 2013/0238021 A1 | 9/2013 | Gross et al. |
| 2013/0238022 A1 | 9/2013 | Gross et al. |
| 2014/0137713 A1* | 5/2014 | Yoshida ................... G01N 1/06 83/15 |
| 2015/0045831 A1 | 2/2015 | Brock |
| 2017/0189016 A1 | 7/2017 | Gross et al. |

OTHER PUBLICATIONS

International Search Report and Written Opinion dated Oct. 25, 2017 for Application No. PCT/US2017/041565, 10 pgs.

\* cited by examiner

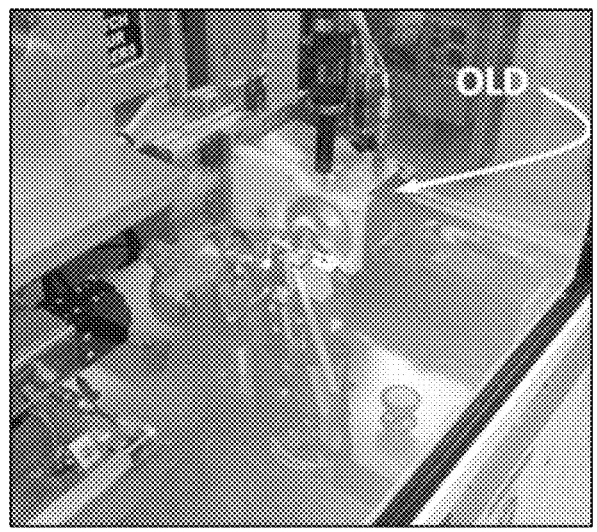
FIG. 6 *PRIOR ART*
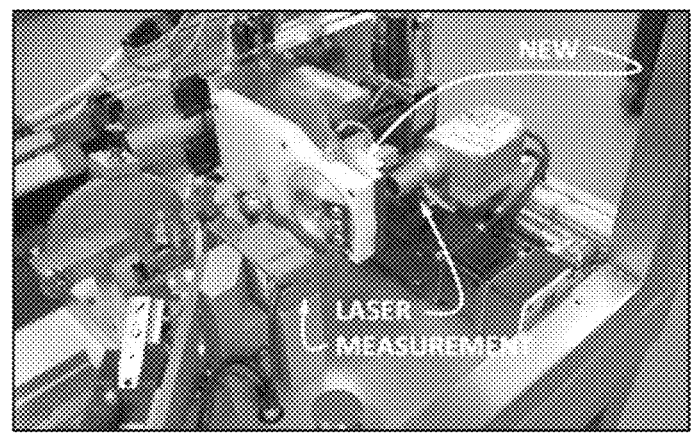
FIG. 7

METHOD AND APPARATUS FOR FABRICATING SELF-RETAINING SUTURES WITH CALIBRATION

CROSS REFERENCE TO RELATED APPLICATIONS

This application claims the benefit of U.S. Provisional Application 62/361,647, filed on Jul. 13, 2016, the content of which is incorporated by reference herein in its entirely.

FIELD

The examples herein relate to methods and apparatuses for forming self-retaining sutures with enhanced calibration. The methods and apparatuses described herein allow a user to control the formation of self-retaining sutures with precision and accuracy, even over time and after blade changes.

BACKGROUND

Self-retaining sutures (sometimes referred to as "barbed sutures") are known, and these sutures are quite helpful in providing secure holding of tissue in various procedures. Self-retaining sutures generally are sutures that have a plurality of retainers, or barbs, on their outer surfaces. In some sutures, these retainers are formed by cutting into the outer surface of a suture to a desired depth and angle, forming a cut portion, which remains secured to the suture at its base. This cut portion typically has a pointed end, which catches tissue when pulled in an opposite direction.

Devices for forming self-retaining sutures are also known, including, for example, those described in U.S. Pat. No. 6,848,152 and U.S. Pat. No. 8,615,856. Apparatuses include, among other features, a device to feed a length of suture through a cutting apparatus, and a blade that intermittently cuts into the suture. In devices, such as that of U.S. Pat. No. 8,615,856, the blade rotates around a central axis, where it cuts into the outer surface of a suture at regular intervals.

During use, as the blade is repeatedly cut into sutures, the blade's configuration may change. For example, the blade may become dull, or it may become heated and warped. Further, although the blade is held securely in place, over use, the blade's position may shift. In addition, the blade may need to be changed repeatedly, and the user may not position the new blade perfectly. Even slight warping or shifting can cause the blade to cut the suture in undesired fashions. As such, it is helpful to have a device and method that can monitor the blade's position and configuration, alerting a user to defects or even controlling the blade position to account for defects.

BRIEF DESCRIPTION OF THE FIGURES

FIG. 6 is a photograph of a cutting apparatus.

FIG. 7 is a photograph of a cutting apparatus according to one or more examples herein.

SUMMARY

Figure 1:
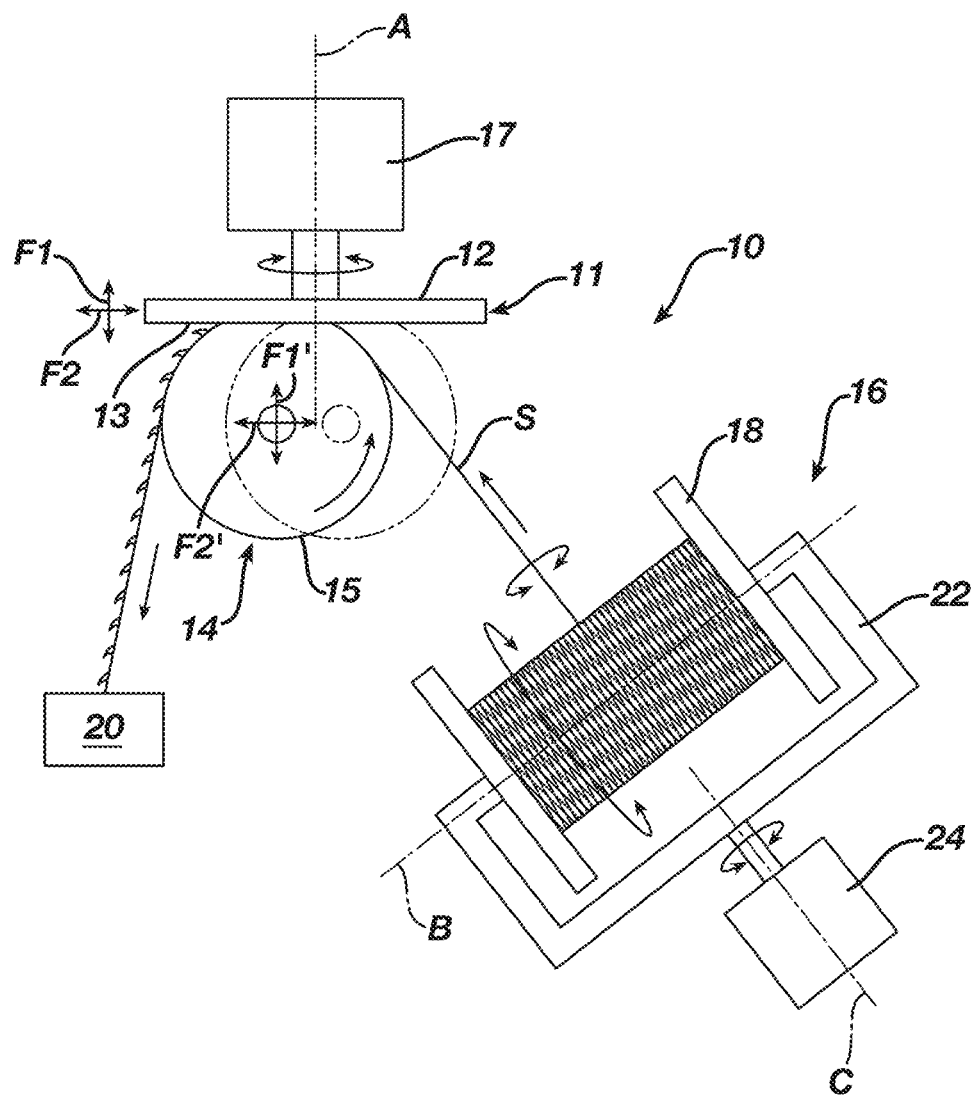
FIG. 1 is a schematic view of a prior apparatus for forming retainers in a strand.

In one example, there is a non-contact method to positively locate the edge position of a cutting blade used in the fabrication of barbed sutures comprising setting a blade in a blade housing at an initial desired position, the blade housing having a hole through it and defining a measurement axis that extends through the hole, where the blade edge is disposed at least partially into the measurement axis; positioning a light emitting device at a first side of the blade housing and aligned with the measurement axis; positioning a light receiving device at a second side of the blade housing and aligned with the measurement axis, where the blade housing is located between the first side and second side; emitting light along the measurement axis from the light emitting device, through the hole, and received by the light receiving device; and measuring the amount of light received by the light emitting device and providing a calibration value based upon the amount of light received.

Examples herein also include a device for cutting retainers into a suture, comprising: a blade housing for holding a blade such that the blade may be rotatable about the circumference of the blade housing, the blade having a blade edge disposed within the circumference of the blade housing, the blade housing having a measurement hole within its circumference, defining a measurement axis that extends through the measurement hole, where the blade edge may be disposed at least partially into the measurement axis; a measurement devices comprising a light emitting device positioned at a first side of the blade housing and aligned with the measurement axis and an analyzer comprising a light receiving device positioned at a second side of the blade housing and aligned with the measurement axis, where the blade housing may be located between the first side and second side, and where the analyzer (e.g., via components therein such as the light receiving device and/or a processor in communication therewith or other computing devices)

may be configured to measure the amount of light received by the light emitting device and provide a calibration value based upon the amount of light received.

Description

The term "tissue retainer" (and variations thereof such as, for example, "retainer" or "barb") as used herein, may refer to a point or pointed part projecting from a strand such as, for example, a suture element having a retainer body projecting from the suture body and a retainer end adapted to penetrate tissue. Each retainer is adapted to resist movement of the suture in a direction other than the direction in which the suture is deployed into the tissue by the surgeon, by being oriented to substantially face the deployment direction (i.e. they lie substantially flat when pulled in the deployment direction; and open or "fan out" when pulled in a direction contrary to the deployment direction). As the tissue-penetrating end of each retainer faces away from the deployment direction when moving through tissue during deployment, the tissue retainers should not catch or grab tissue during this phase. Once the self-retaining suture has been deployed, a force exerted in another direction (often substantially opposite to the deployment direction) causes the retainers to be displaced from their deployment positions (i.e. resting substantially along the suture body), forces the retainer ends to open (or "fan out") from the suture body in a manner that catches and penetrates into the surrounding tissue, and results in tissue being caught between the retainer and the suture body; thereby "anchoring" or affixing the self-retaining suture in place.

The term "retainer configurations" (and variations thereof such as, for example, but not limited to "barb configurations") may refer to configurations of tissue retainers and can include features such as size, shape, surface characteristics, and so forth.

The term "blade" (and variations thereof), as used herein, may refer to the cutting part of a sharpened tool or member.

The term "one-way self-retaining suture" (and variations thereof such as, for example, but not limited to "one-directional suture," "one-directional self-retaining suture," "one-way suture," "uni-directional self-retaining suture," or "uni-directional suture") may refer to a suture having retainers (e.g., barbs) on its exterior surface and facing towards one end of the suture. Such arrangement of retainers on the suture may allow the suture to be drawn in only one direction through tissue, but not in the opposite direction.

The term "two-way self-retaining suture" (and variations thereof such as, for example, but not limited to "two-way suture," "two-directional self-retaining suture," "two-directional suture," "bi-directional self-retaining suture," or "bi-directional suture") may refer to a suture that has retainers (e.g., barbs) facing toward one end of the suture over a portion of the suture length and retainers (e.g., barbs) facing the opposite direction toward the other end of the suture over another portion of the suture length. This arrangement may allow the retainers to move in the same direction as each respective suture end is inserted into host tissue. A bi-directional suture may typically be armed with a needle at each end of the suture thread. Many bi-directional sutures may have a transitional segment located between the two retainer orientations.

The term "suture diameter" may refer to the diameter of the body of the suture. It is to be understood that a variety of suture lengths may be used with the sutures described herein and that while the term "diameter" is often associated with a circular periphery, it is to be understood herein to indicate a cross-sectional dimension associated with a periphery of any shape. Suture sizing is typically based upon diameter. United States Pharmacopeia ("USP") designation of suture size runs from 0 to 7 in the larger range and 1-0 to 11-0 in the smaller range; in the smaller range, the higher the value preceding the hyphenated zero, the smaller the suture diameter. The actual diameter of a suture will depend on the suture material, so that, by way of example, a suture of size 5-0 and made of collagen will have a diameter of 0.15 mm, while sutures having the same USP size designation but made of a synthetic absorbable material or a non-absorbable material will each have a diameter of 0.1 mm. The selection of suture size for a particular purpose depends upon factors such as the nature of the tissue to be sutured and the importance of cosmetic concerns; while smaller sutures may be more easily manipulated through tight surgical sites and are associated with less scarring, the tensile strength of a suture manufactured from a given material tends to decrease with decreasing size. It is to be understood that the sutures and methods of manufacturing sutures disclosed herein are suited to a variety of diameters, including without limitation 7, 6, 5, 4, 3, 2, 1, 0, 1-0, 2-0, 3-0, 4-0, 5-0, 6-0, 7-0, 8-0, 9-0, 10-0 and 11-0.

In self-retaining suture apparatuses, including rotational apparatuses such as those described in U.S. Pat. No. 8,615,856, the forming apparatus will include a suture holder, such as an input spool, which feeds a suture into and through a cutting device. The retainer forming device may have a blade, and there may be a support member arranged adjacent to the blade, where the suture rests against the support member as the blade engages the suture. In rotational apparatuses, the retainer forming device may be arranged to be rotatably driven about an axis (A) by a first rotary drive device (e.g., an electric, pneumatic, hydraulic, or magnetic servo motor) and may include a main body with the blade attached to the main body. The blade may have a cutting edge directed substantially inward toward the axis (A). A feed mechanism may be arranged to support the input spool which supplies a continuous strand of suture material S to the support member such that the retainer forming device can form retainers on the strand S. A take-up mechanism may be arranged to pull the continuous strand S from the input spool about an outer surface of the support member.

Figure 2:
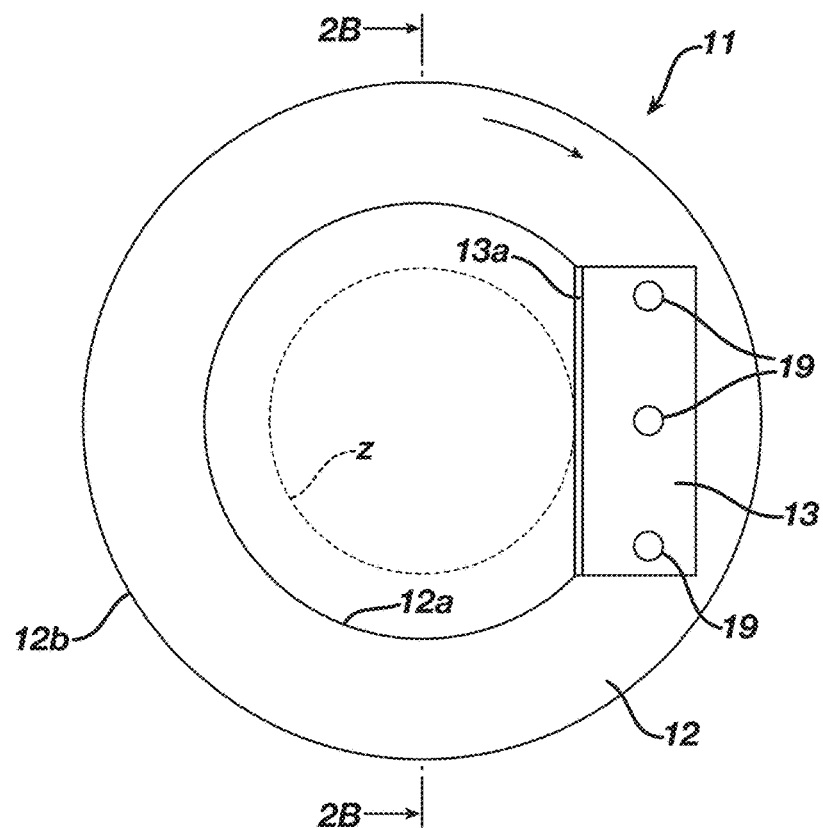
FIG. 2 is a schematic bottom view of the retainer forming member of FIG. 1.
Figure 3:
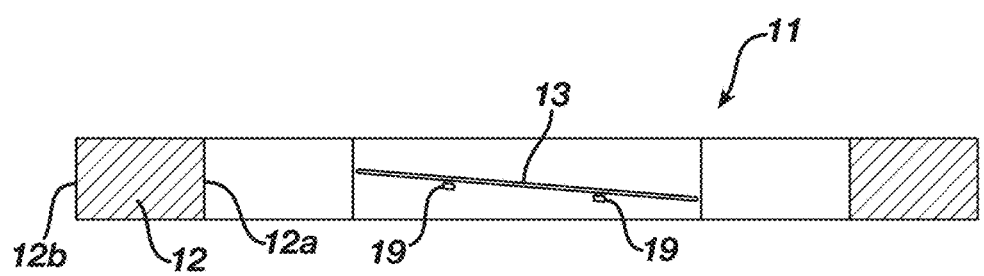
FIG. 3 is a cross-sectional side view of the retaining forming member of FIG. 2 as taken through line 2B-2B.

FIGS. 1-3 represent one embodiment of a prior suture-forming apparatus. As can be seen, the apparatus 10 may include a retainer forming member 11, and support member 14 arranged adjacent to the retainer forming member 11. The retainer forming member 11 may be arranged to be rotatably driven about an axis A by a first rotary drive device 17. The retainer forming member 11 may include a main body 12 with a blade 13 secured thereto. The blade 13 has a cutting edge directed towards the axis A. A feed mechanism 16 may be arranged to secure an input spool 18 to supply a continuous supply of suture material S to the support member 14 where it can be cut by the blade 13. A take-up mechanism 20 may be used to pull the suture strand S. The outer surface 15 of the support member 14 may include a channel or groove for holding the strand S such that the strand S protrudes outwardly from the channel, giving an exposed surface into which the blade may cut. In FIGS. 2-3, the retainer forming member 11 is depicted as a circular ring having the blade 13 secured to the body 12 by fasteners 19 and may be secured in place in grooves in the body 12. The blade 13 may be angled or tilted relative to the plane of rotation as seen in FIG. 3. This configuration may provide desired lifting action as the blade contacts and slices through the strand S as each retainer is cut.

The continuous strand S may be wound about the input spool. The input spool may be supported by a frame such that the input spool is freely rotatable about an axis B to allow the strand S to be unwound therefrom. The frame may also be arranged to be rotatably driven about another axis C by a second rotary drive device (e.g., an electric, pneumatic, hydraulic, or magnetic servo motor). Axis C may be perpendicular to the axis B or have another relative angle. When the second rotary drive device rotates the frame about axis C, the strand S may become twisted about its own central axis as it is unwound from the input spool. Twisting the strand allows for the retainers to be formed with a helical or staggered configuration without twisting or rotating the strand during the cutting cycle itself.

In operation, rotary drive device may rotate the frame about axis C while strand S is pulled by a take-up mechanism, pulling the strand toward and into the retainer forming device. Strand S may unwind from the input spool in a helically twisted state or it may unwind in an untwisted state, and may be received and supported on an outer surface of the support member as it travels toward the take-up mechanism. Support member may be an anvil or a sheave which is rotatable about an axis extending perpendicular to the axis A. The outer surface of the support member may include a channel or groove (as explained above) for receiving the strand S and holding it securely in place.

As explained in the aforementioned patent, the retainer forming member and the support member may be moveable relative to one another in at least two directions. For example, retainer forming member 11 may be moveable in one or both of directions F1 and F2 as shown in FIG. 1 to position the passing strand S such that retainers can be continuously or intermittently formed thereon by the blade 13 of the retainer forming member 11 during rotation of the retainer forming member 11 about axis A. Alternatively, support member 14 may be moveable in one or both of directions F1' and F2' as shown in FIG. 1 to position the passing strand S such that retainers can be continuously or intermittently formed thereon by the blade 13 of the retainer forming member 11 during rotation of the retainer forming member 11 about axis A. Thus, although the support member 14 is shown in FIG. 1 as having an alternative position relative to the retainer forming member 11 (denoted by a dotted outline), either one of the retainer forming member 11 and support member 12 may move relative to the other to position the strand S as necessary for cutting. Such relative movement may provide the apparatus 10 with the ability to engage and disengage the blade 13 from contact with the strand S as well as vary the depth and angle of cut and the retainer direction (i.e., left-hand retainer versus right-hand retainer). Additionally, any relative motion changing the depth of the cut can be used, such as, for example, moving the retainer forming member 12 or support member 15 along an axis extending into or out of the page according to the view shown in FIG. 1. The angle of cut may be changed, for example, by moving the retainer forming member 12 along axis A and re-adjusting the depth of cut. In general, the members 12 and 15 can be moved in many degrees of freedom relative to one another to achieve different cutting properties.

The outer surface of the strand S can be cut by the blade at desired locations. For example, the suture may extend through the retainer forming device such that the blade makes contact with the surface at regular intervals. A continuous helical retainer about the outer surface of the strand S may be cut by a rotating blade making continuous contact with the suture so long as the pitch is very tight, e.g., thread-like, or by keeping the blade stationary and rotating the strand S at high speed, similar to thread cutting on a lathe. Additionally, the angle of the blade with respect to the plane of rotation of the retainer forming member may vary to provide different types of cutting action and, as a result, differently shaped retainers as may be desired.

In order to achieve good cutting action, the blade may be positioned to simultaneously slide across the strand S as it penetrates the strand S during rotation to define a smooth slicing motion. In order to achieve high speed, the retainer forming member may rotate in unidirectional rotary motion about axis A. Any reciprocation motion (linear or rotational) may induce vibration, larger forces, and, as a result, operational speed may be limited. Rotation of the retainer forming member about the circumference of the axis may be achieved as the strand S is pulled through the retainer forming apparatus, or the strand may be pulled a certain length and stopped as the blade cuts into the suture.

The continuous strand S can be helically twisted about its own axis by rotary drive device such that when the blade of the retainer forming member cuts retainers into the passing continuous strand S along a line extending parallel to the axis of the strand S, the strand S can then be untwisted so that the retainers formed thereon may extend along the length of the strand S in a substantially helical configuration.

In another embodiment of the apparatus (not shown), the retainer forming member may have a blade with a cutting edge directed substantially outward away from the axis about which the retainer forming member rotates. The support member may be positioned adjacent to the retainer forming member and the support and/or retainer forming members may be moveable relative to one another. The blade may be unidirectionally rotated about the axis to cut retainers in a continuous strand of suture material passing over the support member.

In a twist-cut method, after cutting is complete, the suture S is untwisted to reveal a plurality of retainers formed helically along the length of the strand S. The retainers may be positioned along the length of the strand S in a helical configuration to define, for example, a one-way self-retaining suture.

The aforementioned process and apparatus describes generally a method of cutting into the outer surface of a suture strand S. Examples herein provide improved devices and methods of achieving cutting to provide for accurate and secure retainer formation over a length of time.

During cutting, the blade slices into the suture about twenty to about 60 times per second, and more specifically about 40 to about 50 times per second, which creates a number of possible issues to the blade. First, given the repeated cutting, the blade may experience wear-down or dulling. Second, there may be heat generated during the process, which can warp the blade's edge. Further, given the number of moving parts and the energy applied, there may be some degree of movement or misalignment of the blade's edge. In addition, it may be desired that the blade be replaced with a fresh blade at regular intervals. Although there may be an initial alignment of the new blade in the device, this alignment may not be perfect and during use, the blade may shift. Any number of factors may come into play, which ultimately result in imperfect blade edge positioning.

Examples herein seek to cure such defects, by analyzing the blade edge position, determining the position and scope of the edge, and either alerting a user to modify the blade position or by controlling the position of one or more of the suture, the blade, the rotating head, or the support member with respect to each other. Although examples herein discuss the use of laser calibration and measurement to control such defects, alternative methods may be used either alone or in combination with the laser calibration methods described herein. Such other methods may include, for example, using visual analysis (such as video measurement) or contact methods, such as where the blade is contacted with a device to measure its position, curvature, and cutting ability. It is less desirable to use contact methods due to a risk of additional defects due to the contact, but these methods are contemplated along with those described herein.

Figure 4:
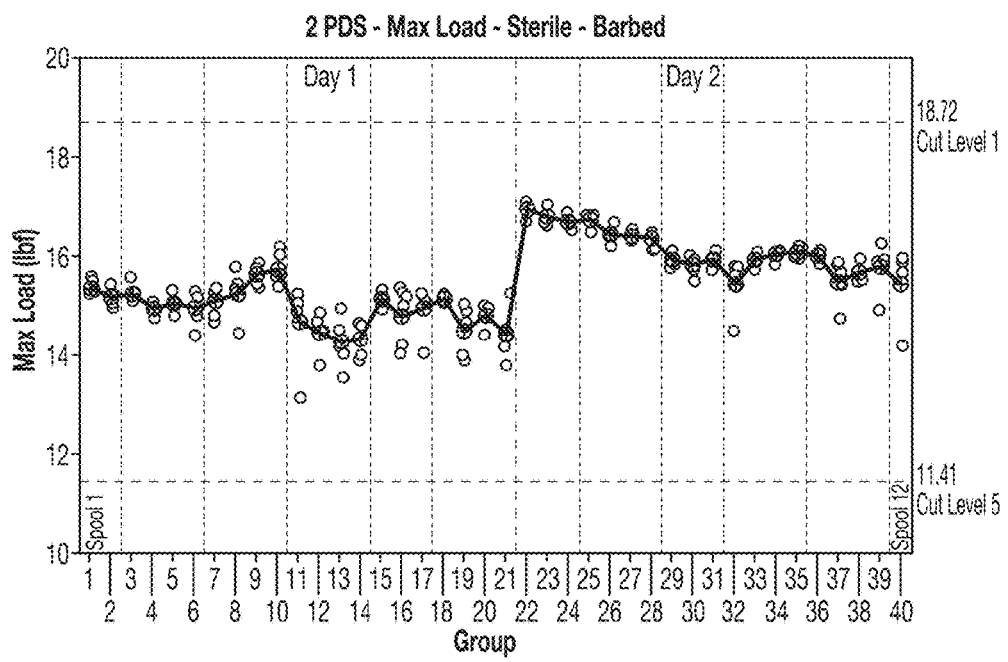
FIG. 4 is a graphical depiction of tests conducted on self-retaining sutures prepared by a prior cutting apparatus.

FIG. 4 depicts an analysis of tensile strength of a barbed suture over the course of a run. The suture tested was a size 2 PDS suture, which was cut using a traditional rotational cutting apparatus, similar to that described above. Each vertical dashed line represents a change in spool of suture, while the center vertical dashed line represents a change in the day (day 1-day 2). As can be seen, the first runs in day 1 provided an average tensile strength of about 15.75 lbf, but by the end of the days' runs, the tensile strength was an average of about 14.0 lbf. At the start of Day 2, the tensile strength of resulting barbed sutures was about 16.75 lbf, but by the end of the day the strength had dropped to about 16.0 lbf.

Figure 5:
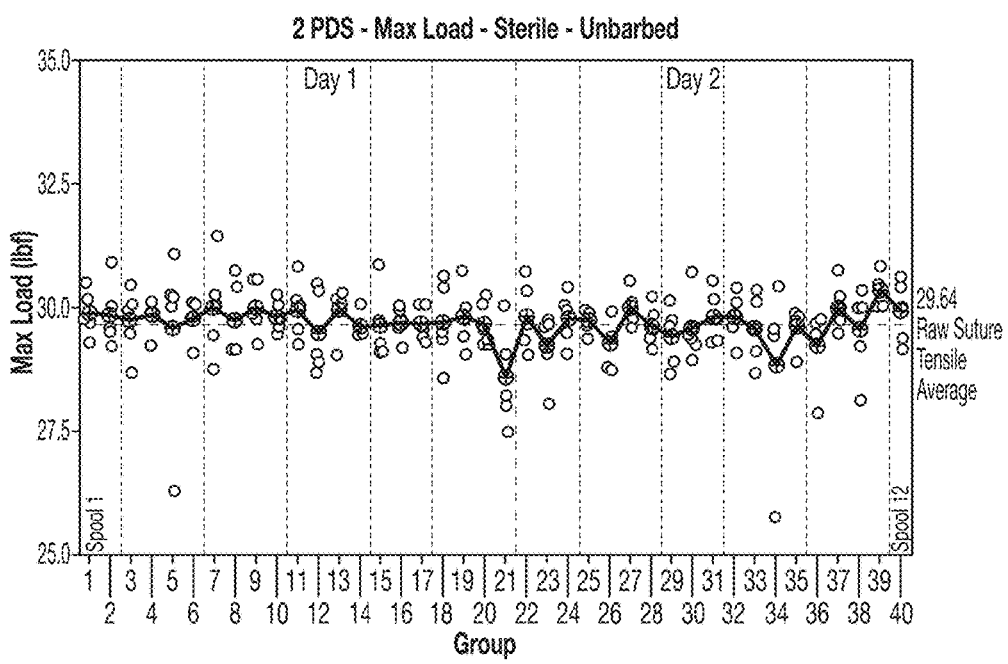
FIG. 5 is a graphical depiction of tests conducted on unbarbed sutures.

The decrease in tensile strength indicated that the barb cut depth was likely increasing as the day went on, as the tensile strength of an unbarbed suture does not show the same trend over time (see FIG. 5). The likely cause of barb cut depth change over time was blade edge position changes, such as due to blade wear, thermal position changes or warping. In addition, as a blade is changed, the position of the blade edge where the cutting occurs could change due not only to user error but also to variation in the blade manufacturing and/or tolerances. Examples herein provide a method and a system to aid in locating and correcting for potential blade edge position changes to assure precision of cut depth over time. In addition, examples herein provide for a more secure and reliable holding for the blade.

As can be seen in FIG. 6, in prior assemblies, such as those described above, a blade housing is provided, along with a suture input assembly, from which a suture strand S can be fed and cut against an anvil. Prior methods relied upon visual aids to ensure proper alignment, cutting and retainer formation. Such methods include, for example, a user visually inspecting the apparatus prior and during cutting to ensure proper alignment. In addition, a camera may be provided to show a larger visual view of the barb after it is formed. Indicia may be provided to allow a user to inspect the size, spacing, alignment and the like. However, these methods do not allow the detailed investigation and review that is helpful in maintaining proper blade edge configurations and alignment on a continuous basis, with the ability to reconfigure position of the blade quickly and accurately. FIG. 7 depicts a configuration of one or more examples herein with improved calibration and measuring tools, including a laser measurement system as will be described below.

Blade Holder Improvement

Examples herein further provide an improved blade holder and bearing and motor support block. The blade holder is attached to a blade spindle and the bearing and motor support block, which sits in a high speed blade spindle drive assembly. The blade holder and spindle assembly is connected to the motor by a series of gears. As the motor rotates, the blade holder and blade rotate around an axis in relation to the cutting anvil. The sharp edge of the blade cuts a barb into the suture during each rotation.

Figure 8:
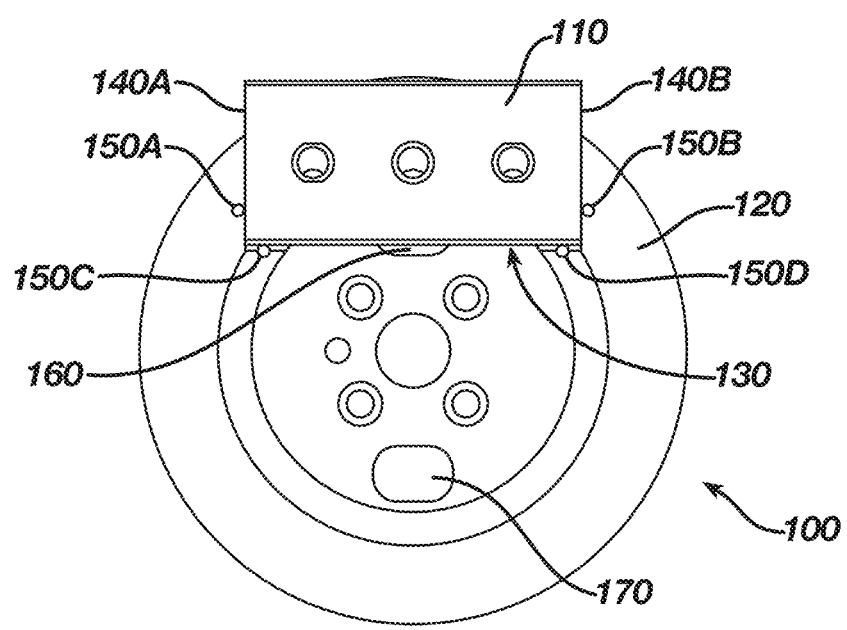
FIG. 8 is a close-up view of a blade housing with a blade housed therein according to one or more examples herein.
Figure 9:
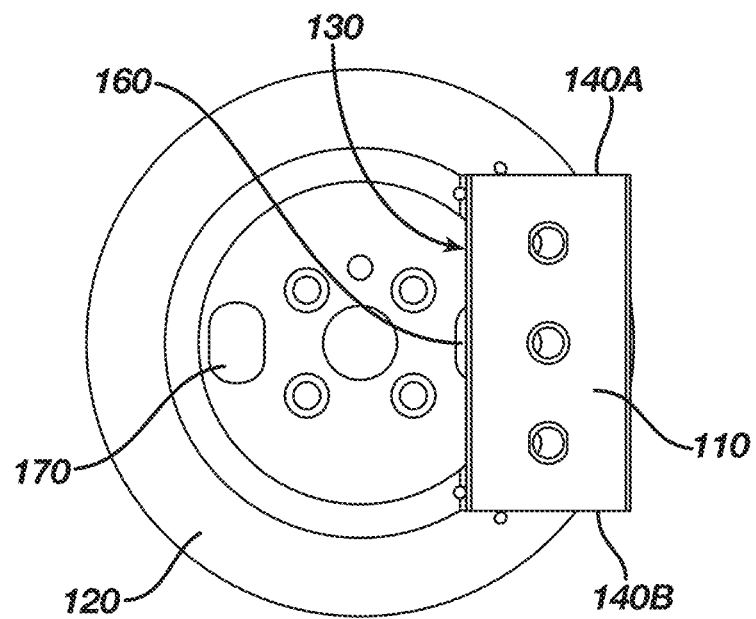
FIG. 9 is a close-up view of the blade housing of FIG. 8 with the blade rotated 90 degrees.

FIGS. 8-9 show one possible configuration for an improved blade holding assembly 100. A blade 110 is secured on the outer circumference of a rotational holding apparatus (a blade holder) 120 with a sharp cutting edge 130 of the blade 110 at least partially disposed within the inner circumference of the blade holder 120. The blade 110 in this aspect is installed in the blade holder 120 with the side edges 140A, 140B of the cutting edge 130 of the blade 110 against at least four locating pins 150A-150D. When the blade 110 is loaded into the device, first side edge 140A of the blade 110 abuts first locating pin 150A, and second side edge 140B of the blade abuts the second locating pin 150B. The sharp edge 130 of the blade 110 abuts third locating pin 150C and fourth locating pin 150D, which are spaced apart from each other a distance less than the length of the cutting edge 130 of the blade 110. As can be seen in FIGS. 8-9, the blade holder 120 includes at least one hole 160, and desirably a first hole 160 and a second hole 170, each disposed on diametrically opposed sides of the blade holder. First hole 160 and second hole 170 pass through blade holder 120, with the first hole 160 at the cutting edge 130 of the blade 110, to provide a clear passageway through blade holder 120.

Figure 10:
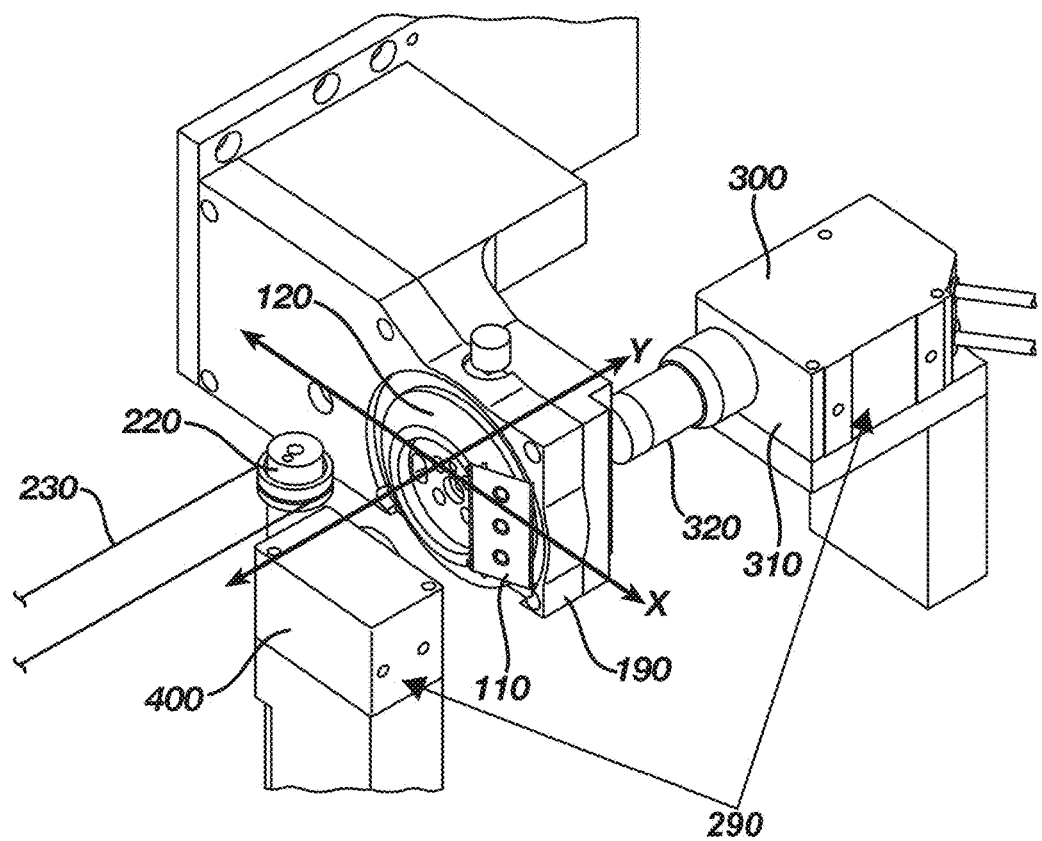
FIG. 10 is a perspective view of an apparatus with the blade and blade holder in the calibration position according to one or more examples herein.
Figure 11:
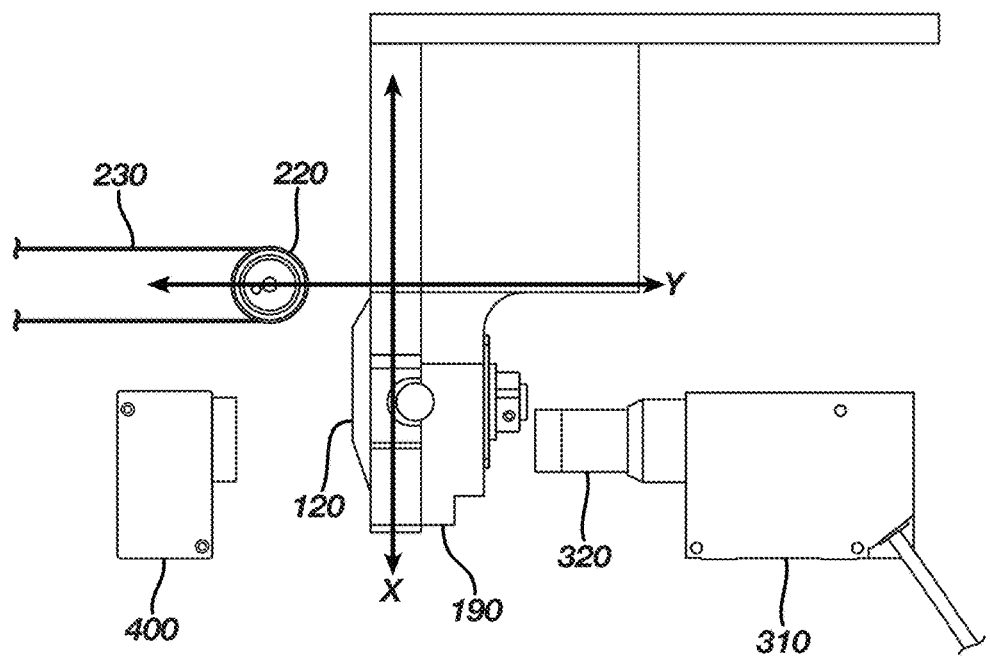
FIG. 11 is a side view of an apparatus with the blade and blade holder in the calibration position according to one or more examples herein.

The passageway through which first hole 160 provides can be defined by axis Y (which is parallel to Axis A in FIG. 1 above). While the first hole 160 and second hole 170 provide several benefits, the first hole 160 is useful in that it provides a clear passageway through the blade housing for a light beam to impact the blade cutting edge 130. The second hole 170 is useful in balancing the blade holder 120. First hole 160 and second hole 170 are aligned such that the sharp edge 130 of blade 110 passes through the axis Y of first hole 160. The alignment of first hole 160 is useful in calibration of the blade edge 130. FIGS. 10-11 show an assembly with respective axis X and axis Y, as will be described in greater detail below.

The blade holder 120 and blade holder housing 190 may also be reduced in mass to help with thermal effects on blade positioning. Since the blade holder 120 and bearing and motor block are connected to the high speed blade spindle drive assembly which is positioned by linear slides in the x-y plane in relation to the cutting anvil 220, the heat from the rotational movement of the blade holder 120 can cause the bearing and motor block to experience a temperature increase. This temperature increase can cause dimensional changes in the position of the blade edge 130, even when the linear slides move the assembly to the same X-Y position, thereby changing the position of the blade 110 in relation to the anvil 220. Even minimal heat variation can cause a significant misalignment of the blade 110 and its edge 130 with respect to the strand 230 into which it will cut retainers. Given the small sizes of suture strands 230 and retainers, even slight misalignment may cause significant differences.

Laser Calibration Device

FIG. 7 is a photograph of an improved assembly in accordance with one or more examples herein. As can be seen, the device described herein includes general features of prior devices described above, including, for example, a rotational blade holder 120, and an anvil 220 against which the suture may be cut. The blade holder 120 may be moved in several different directions, as will be described in greater detail below. The assembly also includes a measurement device 290, which may be optical, such as laser or LED light technology. Measurement device 290 includes a first part or portion 300 and second part or portion 400, the first part or portion 300 including a light generating device 310 and light direction device 320, such as a lens. As will be described below, the light source leaves first part 300 and travels through the blade holder 120, where the light is captured and analyzed by the second part 400, which is an analyzer. The first part 300 and second part 400 of the measurement device are disposed to be axially aligned with each other, with the blade housing 120 disposed between the first 300 and second part 400. Second part 400 (the analyzer) may be in communication with an output device, such as a computer or other machine to provide analyzed results to a user.

With reference to FIGS. 10-16, an apparatus for calibrating the blade edge, and a method for calibrating the blade edge, are described. The figures generally depict a cutting apparatus including a rotating blade holder 120, blade holder housing 190, blade 110, anvil 220, and take-up. The apparatus of these figures further show a measurement device, including first part or portion 300 (e.g., an energy-emitting device) and second part or portion 400 (an analyzer). The first part or portion 300 includes an energy transmitting component 310 or a device such as a light, LED, laser, and/or the like configured to transmit or output energy such as a laser, light, and/or the like and an energy directing component 320, such as a lens or other device for directing energy, such as light, to the analyzer 400. The analyzer 400 includes a receiver or receiving device, such as a charge coupled device (CCD). The receiver or receiving device can also include lens, camera, and/or other devices configured to capture energy such as a light, laser, and/or the like from the components 310 and 320 and/or a processor, memory or a storage device, and/or the like configured to determine the amount of energy or light received from the transmitter or energy component by the receiver and calculate a calibration value based thereon. The energy component and the receiver (such as a Keyence LS-7010) are axially aligned with each other along the Y axis.

Blade holder housing 190 can move in various directions, including the X and Y axes, seen in FIGS. 9-10. It is desired that the blade 110 can be rotated about the circumference of the blade holder 120, while the central region of the blade holder 120 remains constant. For example, the center of the blade housing 120, defining a measurement axis, remains substantially constant throughout the measurement process, and the only movement is the rotation of the blade 110 about the circumference of the blade holder 120. This defines a set measurement axis (along axis Y), along which light is emitted, providing the ability to calibrate the blade 110, and in particular, the blade edge 130, as the blade rotates.

FIGS. 10-11 show the apparatus in a calibrate position. When calibration of the device is desired, the user initiates calibration, and the high speed blade spindle assembly, including blade holder housing 190 moves in various directions to locate the blade housing 120 into the calibrate location or position. The calibrate position is such that the blade edge 130 is disposed approximately halfway between the first part 300 of the measurement device and the second part 400 of the measurement device, but it may be located at any length along the axis Y between the first part 300 and second part 400. As noted above, the blade holder 120 includes a first hole 160, aligned with the measurement axis Y. In the calibrate position, the first part 300 of the measurement device and the second part 400 of the measurement device are aligned with axis Y, such that the first hole 160 is placed within the axial line formed between first part 300 and the second part 400. The blade 100 is installed into the blade holder 120 such that the cutting portion of the sharp edge 130 of the blade 100 is axially aligned with the first 160 hole in the blade holder 120. It is desired that the blade 110 does not fully cover the first hole 160, such that it would effectively block all transmission of light along measurement axis Y.

In the calibrate position, axis Y is aligned substantially with the center of sharp edge 130 of blade 110. Further, given the positioning of the blade 110, some of the light generated by the first part 300 of measurement device may be able to pass through to the second part 400 of measurement device. However, a portion of the light generated by the first part 300 of measurement device is blocked by the blade 110, and does not pass through to the second part 400 of measurement device. The amount of light received by the second part 400 of the measurement device is measured and stored. The blade holder housing 190 can move in various directions during use. In examples, the measurement device 290 can base a calibration value as described herein and/or other components of the apparatus or device based on the amount of light received, for example, as described herein. For example, the measurement device 290 can sent or transmit energy such as light from the first part 300 to the second part 400. The measurement device 290 can then determine the amount of light received by the second part 400 and, based thereon, calculate a calibration value as described herein.

Figure 12:
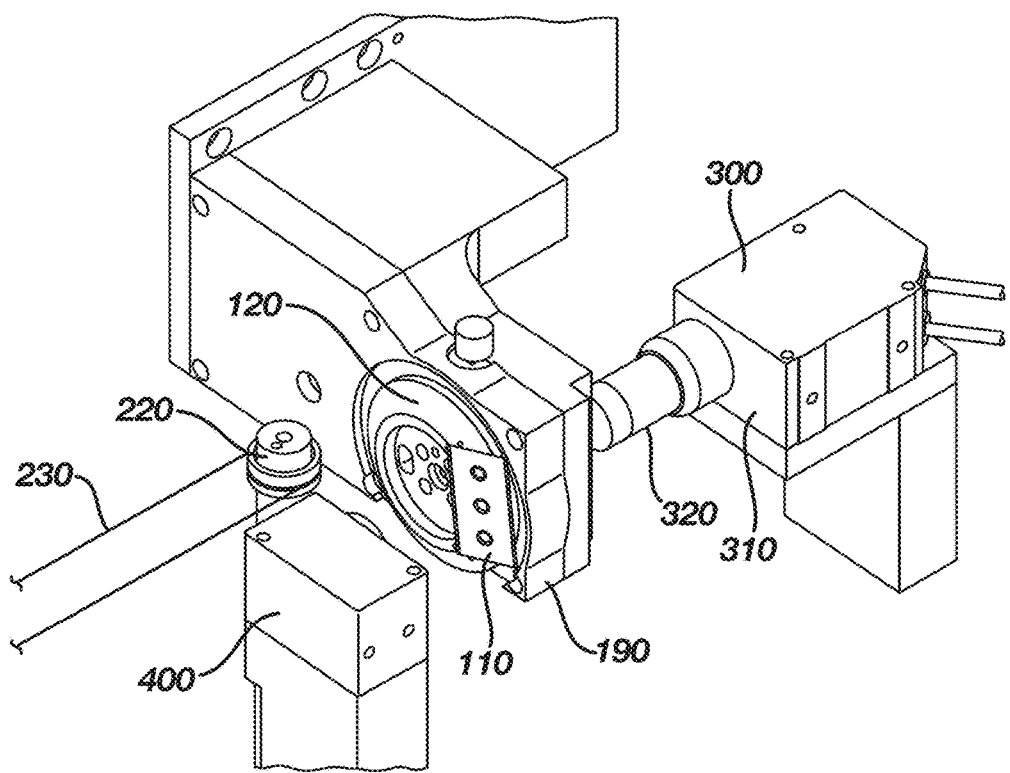
FIG. 12 is a perspective view of an apparatus with the blade and blade holder in the upper position of a calibration sweep according to one or more examples herein.

Once located in the calibrate position, the blade holder housing 190 will rotate the blade holder 120, such that the blade 110 is located at an upper position in the calibration sweep. FIG. 12 shows the blade holder in the upper position of the calibration sweep. As can be seen, the blade 110 has been rotated slightly (approximately 7.5 degrees from the position whereby a blade 110 has a vertical alignment) such that the first edge 140A of blade 110 is moved upwards (e.g., counter-clockwise, as viewed in FIG. 11). Upward movement of the blade 110 is useful in positioning the blade 110 into the state position of the calibration sweep, prior to detailed measurements are taken.

Figure 13:
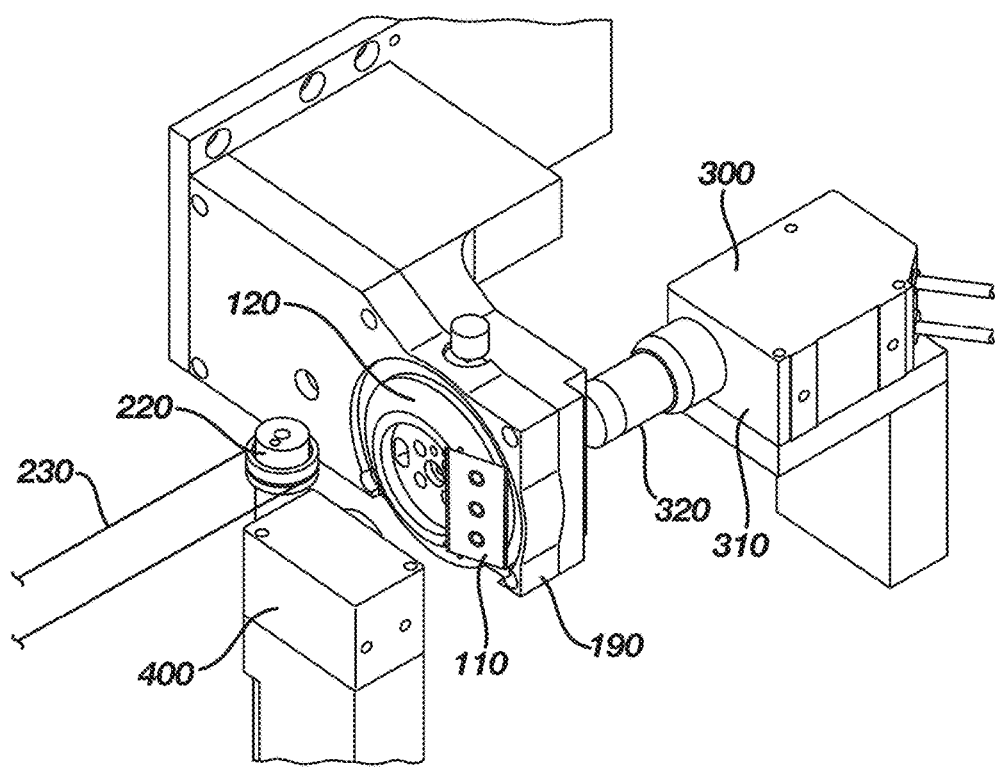
FIG. 13 is a perspective view of an apparatus with the blade and blade holder in the middle position of a calibration sweep according to one or more examples herein.
Figure 14:
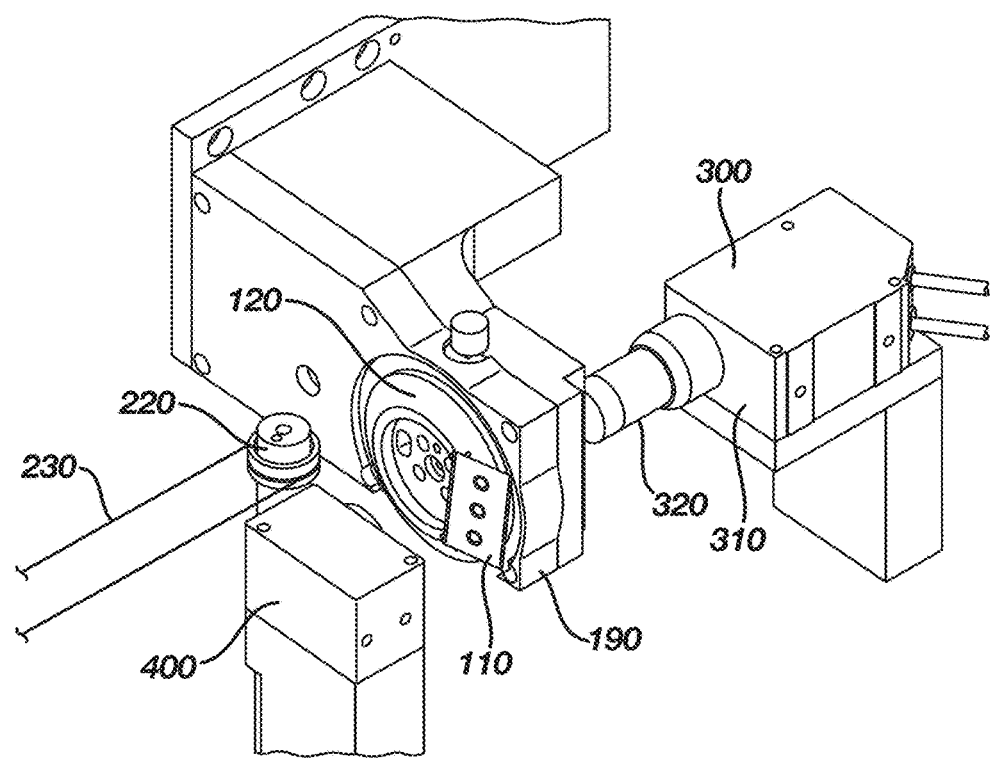
FIG. 14 is a perspective view of an apparatus with the blade and blade holder in the lower position of a calibration sweep according to one or more examples herein.

Calibration then starts by rotating the blade holder 120 in the opposite direction (e.g., clockwise as viewed in FIG. 11) through the calibration sweep of approximately 15 degrees. FIG. 13 shows the blade 110 in the middle position of calibration sweep. When in the middle position, the sharp edge 130 of the blade 110 has an angle that is approximately vertical. FIG. 14 shows the blade in the lower position of calibration sweep. The lower position of calibration sweep is a movement of the blade 110 of about 15 degrees from the start position. The lower position (FIG. 14) should be offset from the middle position (13) by approximately the same amount of rotation as the upper position (FIG. 12). Although the calibration sweep is described herein as being approximately a 15 degree rotation (7.5 degrees counter clockwise from vertical and 7.5 degrees clockwise from vertical), the calibration sweep may be from about 10 degrees to about 45 degrees, as measured from the upper position (FIG. 12) to lower position (FIG. 14).

Thus, the upper position (FIG. 12) may be from about 5 degrees to about 22.5 degrees offset from the middle position (FIG. 13) in a counterclockwise rotation, and the lower position (FIG. 14) may be from about 5 degrees to about 22.5 degrees offset from the middle position (FIG. 13) in a clockwise rotation. During rotation of the blade 110, the first hole 160 remains aligned to the blade 110, allowing a portion of the transmitted energy, such as light, to hit the blade 110 during the full calibration sweep. The blade 110 and the first hole 160 both move through the sweep concurrently, since the blade 110 is affixed to the blade holder 120.

During calibration, the measurement device is active, with energy such as light emanating from the first part 300 to the second part 400, along axis Y. During calibration, the light measurement device measures the high point of the blade edge as it sweeps across the light beam. The system then calculates the blade edge position and compares it to a master reading, where the master reading defines the desired position of the blade edge. The analyzer (such as a computer) takes the comparison and determines a blade correction factor, which is the difference between actual measured position and desired (master) position. As noted above, during use, the blade may become offset for a number of reasons, such as factors including warping, user error, thermal effects, blade to blade variation in manufacturing and blade wearing.

The blade correction factor is used to adjust the blade's position to account for the difference. In some embodiments, the blade needs to be moved in the X direction to adjust blade depth. Movement may be achieved by a user based upon the blade correction factor, or the blade housing may be automatically moved by a computer system. When the system is ready for the next cutting cycle, the offset is now incorporated into the desired position. Movement along the X axis may be performed in real-time, during a cutting cycle, if desired.

Figure 15:
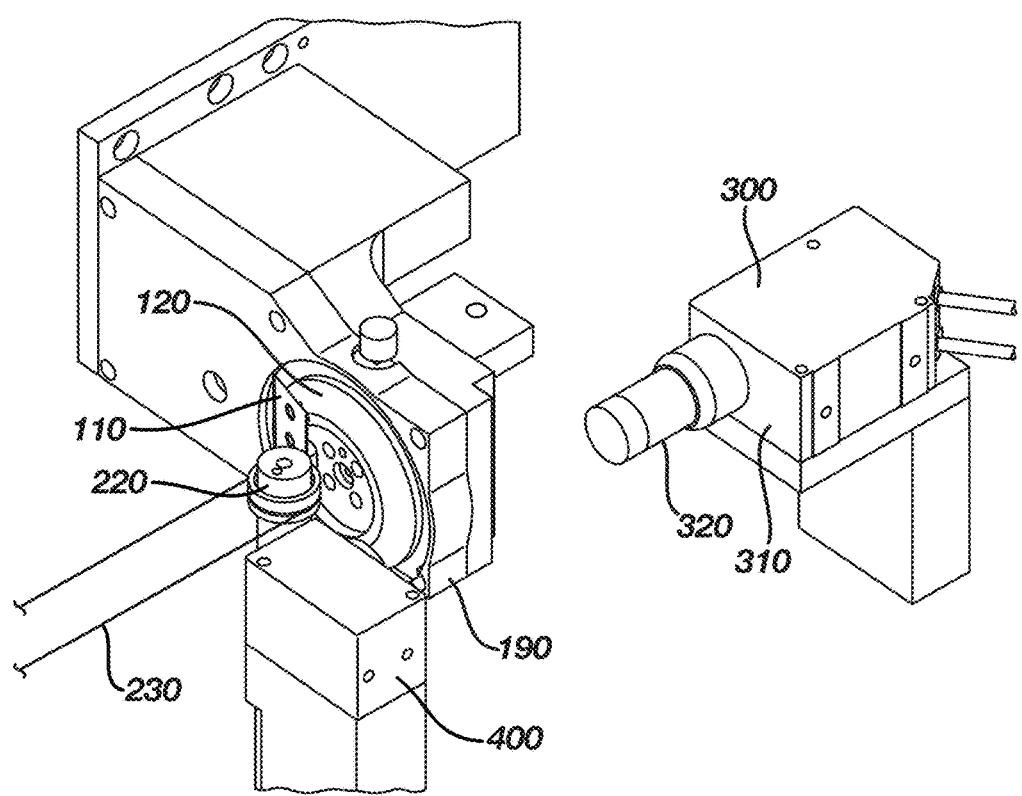
FIG. 15 is a perspective view of an apparatus with the blade and blade holder positioned for a next cut cycle with offset incorporated according to one or more examples herein.
Figure 16:
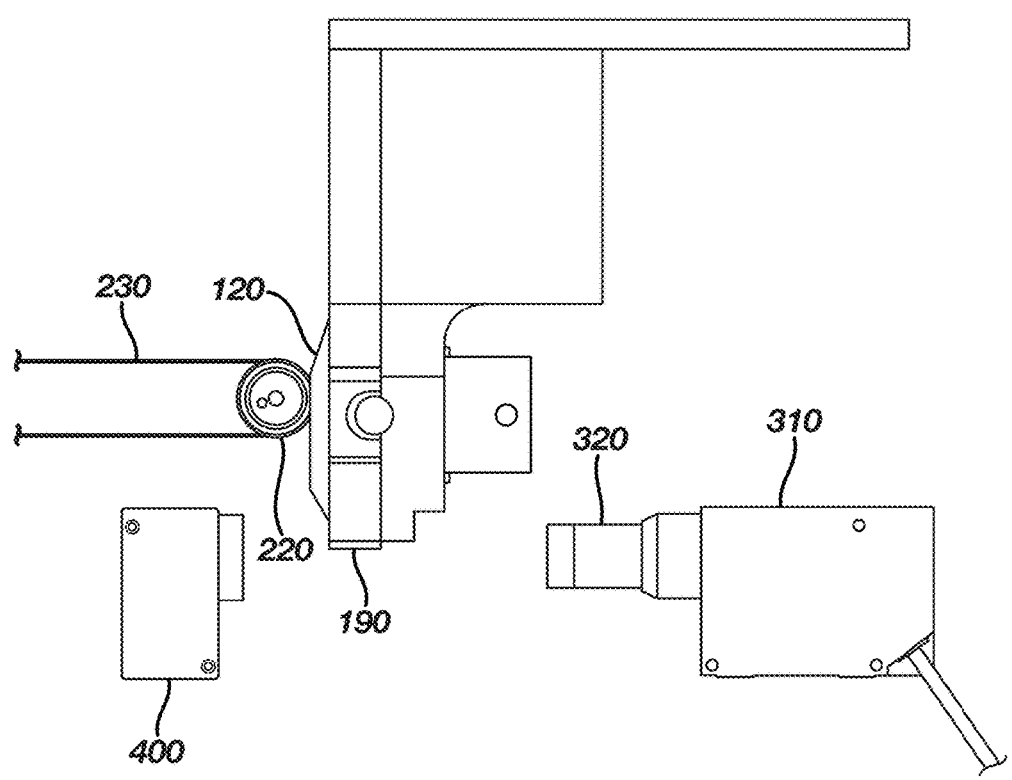
FIG. 16 is a side view of an apparatus with the blade and blade holder positioned for a next cut cycle with offset incorporated according to one or more examples herein.

FIGS. 15 and 16 show the device with the blade located in the Cut 1 ready position (approximately 180 degrees from the calibration position). The blade holder housing 190 moves the blade holder 120 in the x direction towards the anvil 220. Once the suture strand 230 is in the loaded position, the strand 230 being held in place against the anvil 220, and the blade 110 is in the cut position seen in FIG. 15, the rotatable blade holder 120 may rotate and thereby have the blade edge 130 cut into the outer surface of the suture strand 230. Suture strand 230 may be continuously fed around the anvil 220 as the blade 110 is rotated, or suture strand 230 may be fed around the anvil 220 a desired length without the blade holder 120 rotating to create a section of unbarbed suture.

Calibration may be taken prior to starting a new cutting cycle, or after the cutting cycle is complete. Calibration may take place after the blade is changed, or after a suture reel is changed. Calibration may take place after a certain number of sutures have been cut into self-retaining sutures, such as after formation of 30 sutures, or after 50 sutures, or after 100 sutures, by way of example. In some instances, it may be desired to run a calibration after less than 30 sutures are formed, or greater than 100 sutures are formed. It may be desired to use the aforementioned calibration process in addition to a physical measurement of the blade and blade position, such as through contact means or other known methods. Measuring the blade edge 130 physically, such as through contact means, may be useful to apply an initial offset value and may aid in ultimate calibration of the blade position. In addition, it may be useful to use a blade master (which is a carbide block, or other similar material, with a calibrated straight edge) installed in place of the blade 110 to set an initial offset value. The laser device, including first part 300 and second part 400, may be used to do this as well.

Figure 17:
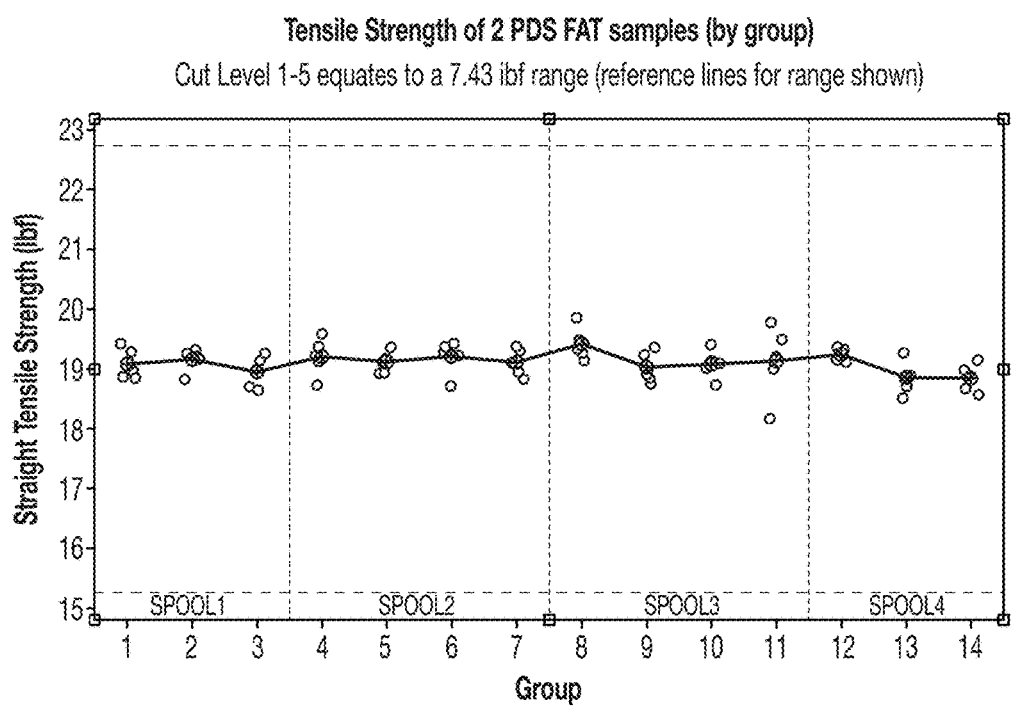
FIG. 17 is a graphical depiction of the testing conducted on self-retaining sutures according to one or more examples described herein.

FIG. 17 shows the results obtained by testing sutures prepared by a device including the measurement device described above. As can be seen, tensile strength of a 2 PDS sample was taken over various cutting cycles. In each result, the tensile strength averaged approximately 19 lbf, with minimal variation over a total of 14 different groups of 25 samples each. The machine was set up with a specific cut depth, and then run continuously (with no adjustment other than changing spools when needed). Each Group on the graph shows the average (and the individual data points) of the first 5 samples of a group of 25 tested for tensile strength. No manual change was made to the Cut Depth setting throughout the run, and at each spool change, the blade calibration routine was performed to capture/offset any blade change.

After measurement of the blade position and spacing, as described herein, the device may provide calibration information to a user, such as through a computer or other readable means, in order to allow the user to make additional adjustments if desired. For example, the user may be alerted to change or adjust the placement of the blade in the housing, or the user may be alerted to shift the blade housing in one or more directions to align the blade with the suture strand in a desired manner.

Examples herein provide a non-contact method to positively locate the edge position of a cutting blade used in the fabrication of barbed sutures including: setting a blade in a blade housing at an initial desired position, the blade housing having a hole through it and defining a measurement axis that extends through the hole, where the blade edge is disposed at least partially into the measurement axis; positioning a light emitting device at a first side of the blade housing and aligned with the measurement axis; positioning a light receiving device at a second side of the blade housing and aligned with the measurement axis, where the blade housing is located between the first side and second side; emitting light along the measurement axis from the light emitting device, through the hole, and received by the light receiving device; and measuring the amount of light received by the light emitting device and providing a calibration value based upon the amount of light received. The method may further include physically measuring blade position by contact means prior to the step of emitting light.

The calibration value may be provided to a user, and the user may use the information provided by the calibration value to adjust the blade or the blade housing. Adjustment may include, for example, movement of the blade housing in one or more axes, or it may include changing the blade or the blade position within the housing. Adjustment may be achieved automatically by the device, based upon the calibration value provided through the measurement described above.

The calibration method may further including a vision system to inspect barbs cut into a suture. For example, the vision system may allow a user to visually inspect the barbs cut into a suture and use the measured barb depth, or barb length, or barb spacing to account for variations by modifying the calibration value.

Examples herein may also include a device for cutting retainers into a suture, including: a blade housing for holding a blade such that the blade is rotatable about the circumference of the blade housing, the blade having a blade edge disposed within the circumference of the blade housing, the blade housing having a central through hole for placement of a suture therethrough, and the blade housing having a measurement hole within its circumference, defining a measurement axis that extends through the measurement hole, where the blade edge is disposed at least partially into the measurement axis; a measurement device comprising a light emitting device positioned at a first side of the blade housing and aligned with the measurement axis and a light receiving device positioned at a second side of the blade housing and aligned with the measurement axis, where the blade housing is located between the first side and second side. In examples, the light receiving device may capture the light, may measure the amount of light received by the light emitting device, and may provide or calculate a calibration value based upon the amount of light received. In other examples, the light receiving device may be included in an analyzer that may have other components such as a processor, a storage component, and/or the like. The light receiving device may capture the light and/or may provide the light or an indication of the amount of light received or captured to the processor and/or a storage component such that the processor may calculate a calibration value based on the amount of light captured or received, which, for example, may be stored in the storage component.

What is claimed is:

1. A non-contact method to positively locate the edge position of a cutting blade used in the fabrication of barbed sutures comprising the steps of:
   i. setting a blade in a blade housing at an initial desired position, the blade housing having a hole through it and defining a measurement axis that extends through the hole, where the blade edge is disposed at least partially into the measurement axis;
   ii. positioning a light emitting device at a first side of the blade housing and aligned with the measurement axis
   iii. positioning a light receiving device at a second side of the blade housing and aligned with the measurement axis, where the blade housing is located between the first side and second side;
   iv. emitting light along the measurement axis from the light emitting device, through the hole, and received by the light receiving device;
   v. measuring the amount of light received by the light emitting device and providing a calibration value based upon the amount of light received.

2. The method of claim 1, wherein the calibration value is provided to a user.

3. The method of claim 2, wherein the user moves at least one of the blade housing or the blade in response to the calibration value.

4. The method of claim 1, wherein at least one of the blade housing or the blade is moved automatically based on the calibration value.

5. The method of claim 4, wherein the movement of the blade housing or the blade includes movement in at least one axis.

6. The method of claim 5, wherein movement of the blade housing or the blade includes movement in at least two axes.

7. The method of claim 1, wherein during the step of emitting light, rotating the blade in blade housing such that the blade edge is moved relative to the measurement axis, and wherein the measurement axis remains constant.

8. The method of claim 7, wherein rotating the blade comprises a first rotation of the blade in a counter clockwise fashion to about 7.5 degrees, followed by rotating the blade in a clockwise fashion to about 15 degrees.

9. The method of claim 7, wherein rotating the blade comprises a first rotation of the blade in a clockwise fashion to about 7.5 degrees, followed by rotating the blade in a counter clockwise fashion to about 15 degrees.

10. The method of claim 1, wherein the light emitted is laser light.

11. The method of claim 1, wherein the light emitted is LED.

12. The method of claim 1, further comprising the step of physically measuring blade position by contact means prior to the step of emitting light.

13. The method of claim 1, wherein calibration by emitting light is performed after the blade has cut about 30 to about 50 sutures.

14. The method of claim 1, wherein calibration by emitting light is performed after the user changes a suture reel.

15. The method of claim 1, wherein calibration by emitting light is performed after the user changes a blade.

16. The method of claim 1, further including a vision system to inspect barbs cut into a suture.

17. The method of claim 16, wherein the user may visually inspect the barbs cut into a suture and use the measured barb depth to account for variations by modifying the calibration value.

18. A device for cutting retainers into a suture, comprising:
   i. a blade housing configured to hold a blade such that the blade is rotatable about the circumference of the blade housing, the blade having a blade edge disposed within the circumference of the blade housing, the blade housing having a measurement hole within its circumference, defining a measurement axis that extends through the measurement hole, where the blade edge is disposed at least partially into the measurement axis;
   ii. a measurement devices comprising:
      a light emitting device positioned at a first side of the blade housing and aligned with the measurement axis;
      an analyzer comprising a light receiving device positioned at a second side of the blade housing and aligned with the measurement axis, wherein the blade housing is located between the first side and second side, and wherein the analyzer is configured to measure the amount of light received by the light emitting device and providing a calibration value based upon the amount of light received.

* * * * *